United States Patent [19]　　　　　　　　　　　　　　　[11]　4,450,958
Prasad　　　　　　　　　　　　　　　　　　　　　　　　[45]　May 29, 1984

[54] SELF-ACTUATED DENTAL CAPSULE

[75] Inventor: Arun Prasad, Cheshire, Conn.

[73] Assignee: Jeneric Industries, Inc., Wallingford, Conn.

[21] Appl. No.: 458,991

[22] Filed: Jan. 18, 1983

[51] Int. Cl.³ .................. B01F 3/12; B65D 25/08; B65D 81/32
[52] U.S. Cl. .................. 206/222; 206/63.5; 206/219; 215/DIG. 8
[58] Field of Search .......... 206/63.5, 219, 220, 206/221, 222, 568; 215/6, DIG. 8; 366/602

[56] References Cited

U.S. PATENT DOCUMENTS

| | | | |
|---|---|---|---|
| 2,487,236 | 11/1949 | Greenberg | 206/47 |
| 2,527,991 | 10/1950 | Greenberg | 206/47 |
| 2,527,992 | 10/1950 | Greenberg | 206/47 |
| 3,043,424 | 7/1962 | Howard | 206/219 |
| 3,139,180 | 6/1964 | Kobernick | 206/47 |
| 3,275,302 | 9/1966 | Horton | 259/72 |
| 3,290,017 | 12/1966 | Davies et al. | 259/114 |
| 3,339,802 | 9/1967 | Weiner et al. | 206/222 |
| 3,357,545 | 12/1967 | Kobernick | 206/47 |
| 3,415,360 | 12/1968 | Baumann et al. | 206/47 |
| 3,425,598 | 2/1969 | Kobernick | 222/83 |
| 3,451,540 | 6/1969 | Kulischenko | 206/47 |
| 3,625,349 | 12/1971 | Muhlbauer | 206/47 A |
| 3,638,918 | 2/1972 | Denholtz | 206/222 |
| 3,651,932 | 3/1972 | Muhlbauer | 206/47 A |
| 3,655,035 | 4/1972 | Muhlbauer | 206/47 A |
| 3,655,037 | 4/1972 | Lussler | 206/635 |
| 3,796,303 | 3/1974 | Allet-Coche | 206/47 |
| 3,815,878 | 6/1974 | Baskas et al. | 259/37 |
| 3,841,467 | 10/1974 | Hansen | 206/219 |
| 3,963,120 | 6/1976 | Perfect | 206/219 |
| 3,986,834 | 10/1976 | Steinbrink, Jr. | 23/230 |
| 4,142,629 | 3/1979 | Biondo et al. | 206/219 |
| 4,182,447 | 1/1980 | Kay | 206/220 |
| 4,185,740 | 1/1980 | Perfect | 206/220 |
| 4,306,651 | 12/1981 | Muhlbauer | 206/219 |

FOREIGN PATENT DOCUMENTS

| | | |
|---|---|---|
| 519008 | 4/1953 | Belgium . |
| 354351 | 6/1961 | Switzerland . |
| 1180181 | 2/1970 | United Kingdom . |
| 2027601 | 2/1980 | United Kingdom . |

Primary Examiner—George E. Lowrance
Assistant Examiner—Jimmy G. Foster
Attorney, Agent, or Firm—Barry Kramer

[57] ABSTRACT

A self-actuated dental capsule is provided which includes a three-part container for holding the liquid component of an amalgam. One part of the container holds the liquid; a second part is used to attach the container along an inner side wall of the capsule so that the container is not repeatedly pounded by the amalgam during the vibratory process; and the third part allows the liquid to achieve sufficient momentum when the capsule is vibrated in a dental amalgamator to rupture the container.

6 Claims, 5 Drawing Figures

SELF-ACTUATED DENTAL CAPSULE

BACKGROUND OF THE INVENTION

1. Field of the Invention

This invention relates to dental capsules and in particular to dental capsules of the self-actuating type.

2. Description of the Prior Art

Dental amalgam fillings are produced by mixing together a liquid component, e.g. mercury, and a powdered component, e.g. silver or a silver alloy. Dental capsules are used both to hold the liquid and powdered components separate from each other during shipping and storage and as a mixing chamber for mixing the liquid and powdered components together to form the amalgam.

Over the years, numerous dental capsules have been proposed. These capsules differ from one another both in the means used to hold the liquid component and in the means used to release this component for mixing with the powdered component. In the past, releasing of the liquid has required some manual manipulation of the capsule by the dentist. For example, in some prior art capsules, it was necessary to rotate a portion of the capsule to release the mercury. Other capsules employed telescoping members whereby the movement of one member past another released the mercury. Other mechanisms, including cutting a sack of mercury with a sharp blade, have been suggested.

Recently, dental capsules which are self-actuating have become available. With these types of capsules, a separate step is not required to release the mercury for mixing with the powdered component of the amalgam. Rather, the mercury is automatically released during vibration of the capsule in an amalgamator.

One such capsule is shown in U.S. Pat. No. 4,306,651. In accordance with this patent, the mercury is encapsulated in a foil bag and the bag and powder are placed together in the dental capsule. When the capsule is vibrated in an amalgamator, the foil bag ruptures allowing the mercury to mix with the powder. This design has a number of drawbacks. For example, a portion of the mercury can remain inside the bag after vibration in the amalgamator, thus causing variations in the chemical composition of the amalgam. Further, the bag tends to stick to the amalgam, resulting in the bag being repeatedly pounded against the walls of the capsule by the amalgam during the vibratory process. This can cause the bag to partially disintegrate so that pieces of the bag become incorporated into the amalgam, an obviously undesirable result. Moreover, because the bag sticks to the amalgam, it must be removed from the amalgam by the dentist before the filling material is inserted in a patient's tooth. Since there is a limited amount of time during which the amalgam can be used after the mercury and the powder have been combined, this extra step of removing the bag from the amalgam is undesirable.

Other prior self-actuated capsules, such as those shown in U.S. Pat. No. 4,182,447, U.K. patent application No. 2,027,601 and Belgium Pat. No. 519,008, have similar problems or are difficult to manufacture.

In view of these problems with the prior art self-actuated dental capsules, it is the object of this invention to provide an improved self-actuated dental capsule which is simple to construct, does not require separating the amalgam from the means used for holding the mercury, insures that all of the mercury is mixed with the silver-containing powder and protects the means used for holding the mercury from disintegration during the vibratory process.

SUMMARY OF THE INVENTION

In accordance with the invention, an improved self-actuating capsule for a dental amalgam which includes a powdered component and a liquid component is provided. The capsule comprises a chamber for holding the powdered component and for mixing the powdered and liquid components to form the amalgam. Disposed within the chamber is a container for the liquid component of the amalgam. The container is self-rupturing and empties completely when the capsule is vibrated in a dental amalgamator.

The capsule and the container for the liquid component are designed so that the container does not become attached to the amalgam during the vibratory process. In this way, the container is not repeatedly pounded against the walls of the capsule by the amalgam and thus does not disintegrate. Also, keeping the container and the amalgam separate from each other avoids the problem of having to separate the container from the amalgam prior to placing the amalgam in a patient's tooth.

Capsules constructed in accordance with the invention comprise the following:

a chamber for holding the powdered component and for mixing the powdered and liquid components together to form the amalgam, the chamber including a side wall and end walls;

a rupturable container for holding the liquid component of the amalgam, the container including a first portion which holds the liquid component, a second portion for locating the container along the side wall of the chamber and for holding the container along that wall as the capsule is vibrated in a dental amalgamator, and a third portion for allowing the liquid component to acquire sufficient momentum to rupture the container when the capsule is vibrated in a dental amalgamator; and means for opening the chamber to remove the amalgam after the powdered and liquid components have been mixed together.

In certain preferred embodiments of the invention, the container is in the form of a continuous, elongated, sealed tube, a first part of which is used to hold the mercury, a second part for locating the tube along a side wall of the capsule, and a third part for allowing the mercury to acquire sufficient momentum to rupture the container when the capsule is vibrated in a dental amalgamator. In a particularly preferred embodiment of the invention, the capsule is composed of two mating sections and the portion of the container for locating the tube along a side wall of the capsule is engaged by the sections in the region where they mate. In connection with this embodiment, one of the sections can include a recess for receiving the portion of the tube used to locate the tube along a side wall of the capsule.

DESCRIPTION OF THE PREFERRED EMBODIMENTS

The present invention provides an easy to construct and easy to use self-actuated dental capsule. In particular, the invention eliminates the need to separate the amalgam from the means used to hold the liquid component of the amalgam, insures that all of the liquid component of the amalgam is incorporated into the amalgam, and protects the container for the mercury from disintegration during vibratory mixing of the amalgam in an amalgamator. Moreover, as described below, construction of the capsule involves only simple to fabricate parts.

Figure 1:
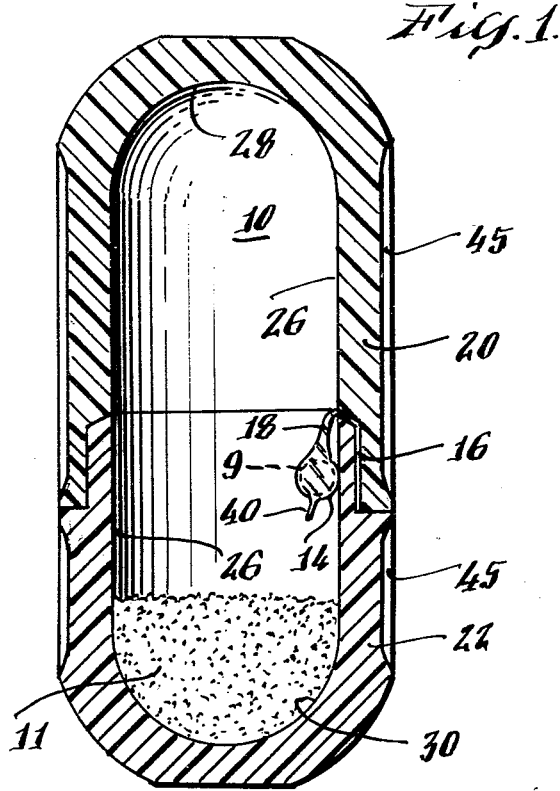
FIG. 1 shows an assembled capsule constructed in accordance with the present invention prior to vibration in a dental amalgamator.
Figure 2:
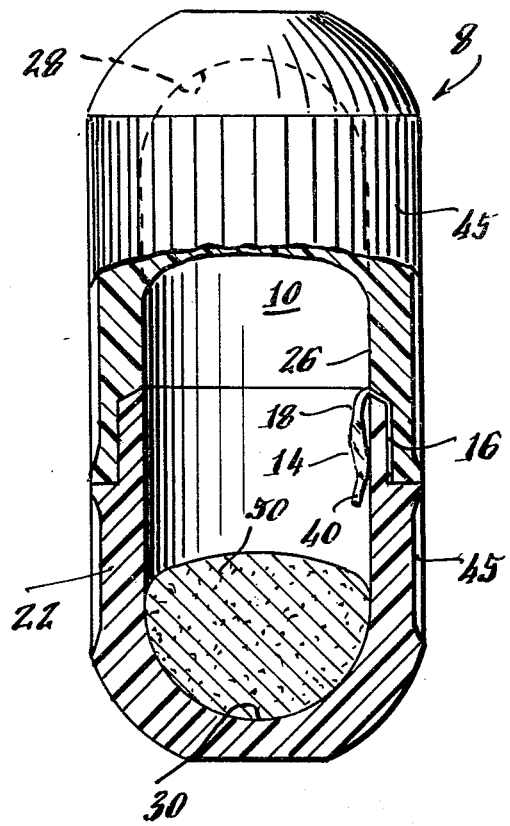
FIG. 2 shows the capsule of FIG. 1 after vibration in a dental amalgamator.
Figure 3:
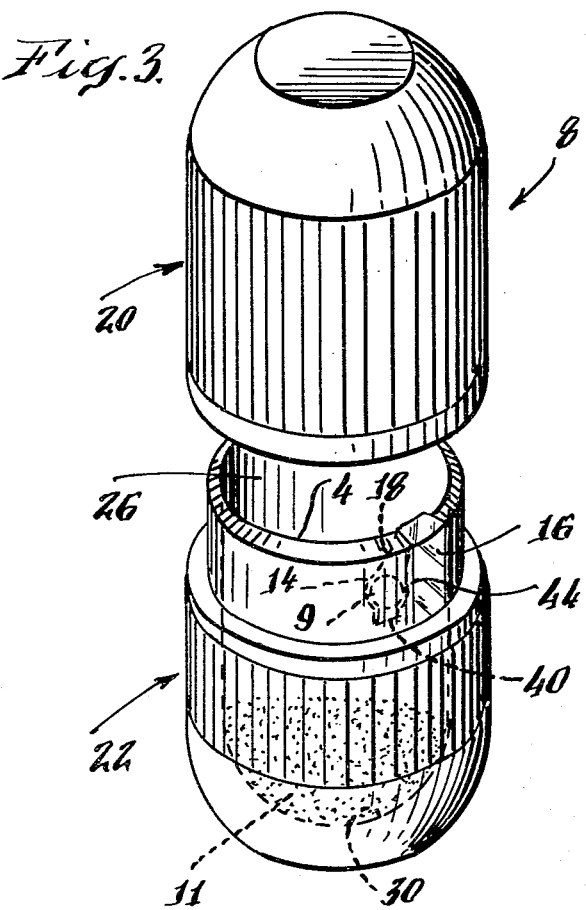
FIG. 3 shows the capsule of FIG. 1 partially assembled.

As shown in FIGS. 1-3, capsule 8 of the present invention includes cylindrically-shaped chamber 10 for holding powdered component 11 of a dental amalgam during shipping and storage and for mixing the liquid and powdered components together to form a dental amalgam. Chamber 10 is composed of side wall 26 and end walls 28 and 30. Capsule 8 is formed from two mating cylindrically-shaped sections 20 and 22 which can be separated for removing amalgam 50 from chamber 10 once the liquid and powdered components have been mixed. Sections 20 and 22 can be molded from a plastic material such as polyethylene or polypropylene. They can include finger ribs 45 to aid in handling.

Figure 4:
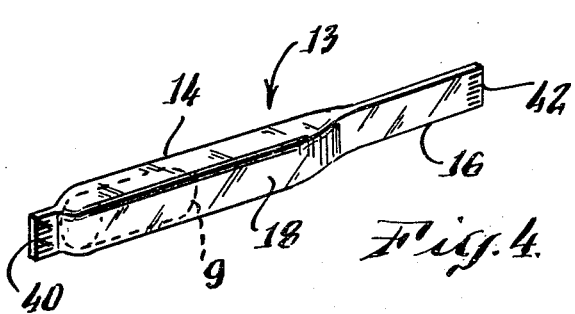
FIG. 4 is a detailed view of the container for the liquid component of the amalgam.
Figure 5:
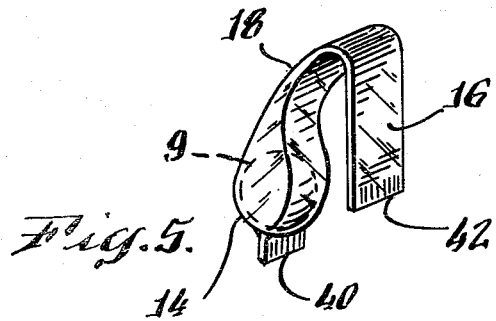
FIG. 5 shows the container for the liquid component of the amalgam just prior to placement in the capsule.

As shown in FIGS. 4 and 5, container 13 for the liquid component of the amalgam includes portion 14 for liquid component 9, portion 16 for locating container 13 along side wall 26 of chamber 10 (see FIGS. 1-3), and portion 18 for allowing liquid component 9 to acquire sufficient momentum to rupture container 13 when capsule 8 is vibrated in a dental amalgamator.

Container 13 is preferably in the form of an elongated, continuous tube which is sealed at its opposite ends 40 and 42. Various materials can be used to construct container 13, including polymeric materials, such as polyethylene, polypropylene, polyamid, polyvinylidene chloride and the like. Metal foils, such as aluminum foil, also can be used, although polymeric materials are considered preferable. Ends 40 and 42 of container 13 can be sealed in a variety of ways, including gluing and heat sealing. Heat sealing of ends 40 and 42 is preferred. Containers formed in this manner have been found to rupture reliably at the heat seal when capsule 8 is vibrated in a dental amalgamator. As shown in FIGS. 4 and 5, portion 16 of container 13 can be flattened for attachment of the container along side wall 26 of chamber 10.

Capsule 8 is assembled in the following manner. First, container 13 is filled with an appropriate amount of the liquid component of the amalgam, e.g., 0.6 grams of mercury, and sealed closed. Sufficient room is left unfilled in container 13 so as to provide portion 16 for locating the container along side wall 26 of chamber 10 and portion 18 for allowing liquid component 9 to acquire sufficient momentum to rupture the container (see FIGS. 4 and 5).

Next, powdered component 11 is placed into section 22 of the capsule 8. Portions 14 and 18 of container 13 are then introduced into section 22. Portion 16 of container 13 is placed along the outside of section 22 with the junction of portions 16 and 18 lying along rim 4 of section 22. As shown in FIGS. 1-3, section 22 preferably includes recess 44 for receiving portion 16 of container 13.

To complete the capsule, section 20 is mated with section 22. In FIGS. 1-3, sections 20 and 22 mate by section 20 sliding over section 22. It is to be understood that other mating arrangements, e.g., screwtype arrangements, can be used to mate sections 20 and 22. Also, container 13 can have configurations other than that illustrated herein and the container can be retained along a side wall of chamber 10 in ways other than that illustrated and the advantages of the present invention, described above, will still result. For example, section 22 need not include recess 44 for portion 16 of container 13. Rather, section 20 can simply be force fitted over section 22 with one or the other of sections 20 and 22 yielding to provide room for portion 16. Similarly, container 13 need not be a continuous tube but can consist of a partially-filled chamber for liquid component 9 connected to a tail or tab for retaining the container along side wall 26 of chamber 10 during the vibratory process.

Once capsule 8 has been assembled, it can be shipped and stored until needed by the dentist. Container 13 prevents liquid component 9 from mixing with powdered component 11 until the time of use of capsule 8. To use capsule 8, the dentist simply inserts the capsule into an amalgamator. The amalgamator vigorously vibrates the capsule causing liquid component 9 to acquire sufficient momentum to rupture container 13, usually along the seal at end 40 of the container. Once container 13 is ruptured, liquid component 9 and powdered component 11 combine and mix together to form the amalgam. During this mixing process, container 13 is held along side wall 26 of chamber 10 and thus is not repeatedly pounded by amalgam 50 during the vibratory process.

After the powdered and liquid components of the amalgam have been thoroughly mixed, capsule 8 is opened by separating sections 20 and 22. The amalgam is then removed from capsule 8 and applied to the patient's tooth.

The following examples further illustrate the various features of the invention. It is to be understood that these examples are not to be construed as limiting the invention in any manner.

EXAMPLE 1

Twenty capsules were constructed having the configuration and components shown in FIGS. 1-5, except that recess 44 for portion 16 of container 13 was not employed, section 20 simply being force-fitted over section 22. The capsules were of the standard size for use in dental amalgamators, that is, they were approximately 3.2 cm long and had a diameter of approximately 1.3 cm. Portion 22 of each capsule was approximately 2.5 cm long and portion 20 was approximately 1.2 cm long. Six-tenths of a gram (0.6 gm) of silver alloy powder were placed into portion 22 of each capsule.

Containers 13 were made from polyethylene having a thickness of approximately 2 mil. The containers were approximately 20 mm long, had a diameter of approximately 5 mm and were heat sealed at each end. Six-tenths of a gram (0.6 gm) of mercury were placed in each container. This amount of mercury occupied about 5 mm of the container leaving approximately 15 mm for portions 16 and 18. Approximately 10 mm of container 13 were placed along the outside of section 22 leaving approximately 5 mm for portion 18.

Each capsule 8 was vibrated for ten to twenty seconds in a Caulk Vari Mix II—m amalgamator (L. D. Caulk Co., Milford, Del.) operated at 53-55 CPS. At the end of the vibration period, each capsule was opened and the amalgam was examined. All containers for the twenty test capsules were found to have ruptured along the heat seal at end 40 and to have completely emptied. The amalgams were found to be completely mixed and suitable for use in a patient's tooth. The containers, although ruptured, were found not to have disintegrated, and no plastic was found intermixed with the amalgams.

EXAMPLE 2

This example illustrates the ability of container 13 to maintain liquid component 9 and powdered component 11 separate during shipping and handling. Twenty capsules were prepared in the manner described in Example 1. Each of these capsules was dropped from a height of four feet onto a concrete floor covered with vinyl tiles. The capsules were then opened and containers 13 examined for evidence of rupture. No damage to any of the containers was found.

In another test, one capsule was dropped four times from a height of four feet onto a concrete floor covered with vinyl tiles. No damage to container 13 was observed for this very abusive test.

Although specific embodiments of the invention have been illustrated, it is to be understood that modifications to the invention can be made without departing from its spirit or scope. For example, the various components of the capsule can have a variety of configurations, sizes and proportions and the components of the capsule can be assembled in ways other than the way illustrated herein.

What is claimed is:

1. A self-actuated capsule for a dental amalgam, said capsule including a powdered component and a liquid component and comprising:
   a chamber holding the powdered component and for mixing the powdered and liquid component together to form the amalgam, the chamber including a side wall and end walls;
   a rupturable container for holding the liquid component of the amalgam, said container including a first portion holding the liquid component, a second portion securing the container along the side wall of the chamber, and a third hollow portion in communication with said first portion for allowing the liquid component to acquire sufficient momentum to rupture the container when the capsule is vibrated in a dental amalgamator; and
   means for opening the chamber to remove the amalgam after the powdered and liquid components have been mixed together.

2. The capsule of claim 1 wherein the capsule includes two mating sections and the second portion of the container is engaged by the sections in the region where they mate.

3. The capsule of claim 2 wherein one of the sections includes a recess for receiving the second portion of the container.

4. The capsule of claim 1 wherein the container is in the form of an elongated tube which is sealed at both ends.

5. The capsule of claim 4 wherein the tube is composed of a polymeric material.

6. The capsule of claim 5 wherein the ends of the tube are heat sealed.

* * * * *